United States Patent
West (10) Patent No.: US 11,504,483 B2
(45) Date of Patent: Nov. 22, 2022

(54) PEN NEEDLE MULTIPLE CARRIER INJECTION SYSTEM

(71) Applicant: Embecta Corp., Andover, MA (US)

(72) Inventor: Robert West, Basking Ridge, NJ (US)

(73) Assignee: Embecta Corp., Andover, MA (US)

(*) Notice: Subject to any disclaimer, the term of this patent is extended or adjusted under 35 U.S.C. 154(b) by 304 days.

(21) Appl. No.: 16/623,277

(22) PCT Filed: Jun. 14, 2018

(86) PCT No.: PCT/US2018/037540
§ 371 (c)(1),
(2) Date: Dec. 16, 2019

(87) PCT Pub. No.: WO2019/005495
PCT Pub. Date: Jan. 3, 2019

(65) Prior Publication Data
US 2020/0179616 A1   Jun. 11, 2020

Related U.S. Application Data (60) Provisional application No. 62/525,448, filed on Jun. 27, 2017.

(51) Int. Cl.
*A61M 5/32*    (2006.01)
*A61M 5/315*   (2006.01)
*A61M 5/34*    (2006.01)

(52) U.S. Cl.
CPC ...... *A61M 5/3295* (2013.01); *A61M 5/31528* (2013.01); *A61M 5/3202* (2013.01); *A61M 5/3276* (2013.01); *A61M 5/345* (2013.01); *A61M 5/347* (2013.01)

(58) Field of Classification Search
CPC ............ A61M 5/3295; A61M 5/31528; A61M 5/3202; A61M 5/3276; A61M 5/345; A61M 5/347; A61M 5/348; A61M 5/3298
See application file for complete search history.

(56) References Cited

U.S. PATENT DOCUMENTS

| | | | |
|---|---|---|---|
| 5,752,936 A * | 5/1998 | Chen | A61B 5/15003 600/576 |
| 5,829,589 A * | 11/1998 | Nguyen | A61M 5/3202 206/366 |
| 5,873,462 A | 2/1999 | Nguyen et al. | |
| 5,931,817 A * | 8/1999 | Nguyen | A61M 5/002 604/263 |
| 6,346,094 B2 | 2/2002 | West et al. | |
| 9,107,988 B2 | 8/2015 | Bruehwiler et al. | |
| (Continued) | | | |

FOREIGN PATENT DOCUMENTS

| | | |
|---|---|---|
| JP | 2000-102614 A | 4/2000 |
| WO | 2012/098767 A1 | 7/2012 |

*Primary Examiner* — James D Ponton
*Assistant Examiner* — Neeraja Gollamudi
(74) *Attorney, Agent, or Firm* — Greenberg Traurig, LLP; David J. Dykeman; Roman Fayerberg (57) ABSTRACT

A multiple carrier injection system includes an adapter, having at least one arm, and a pen needle assembly. The pen needle assembly includes a hub retaining a needle and a bullet having a cover to seal the bullet, where the bullet encloses the hub in a first position. The arm engages the adapter to the hub, and the arm causes the hub to rotate within the bullet to move the hub into a second position.

24 Claims, 6 Drawing Sheets

(56) References Cited

U.S. PATENT DOCUMENTS

| | | |
|---|---|---|
| 9,427,514 B2 | 8/2016 | Bruehwiler et al. |
| 9,642,963 B2 | 5/2017 | Larsen et al. |
| 2001/0014792 A1* | 8/2001 | West ................. A61M 5/347 |
| | | 604/239 |
| 2006/0015066 A1 | 1/2006 | Turieo et al. |
| 2009/0312715 A1 | 12/2009 | Monson et al. |
| 2012/0016315 A1 | 1/2012 | Radmer et al. |

\* cited by examiner

FIG.6
SECTION A-A

PEN NEEDLE MULTIPLE CARRIER INJECTION SYSTEM

This application claims the benefit under 35 U.S.C. § 119(e) of U.S. Provisional Application No. 62/525,448, filed Jun. 27, 2017, the entire content of which is incorporated herein by reference.

FIELD

Various exemplary embodiments of the invention relate to medication pen needles.

BACKGROUND

Medication pens are used to inject medication into a patient. A person who must periodically inject doses of medication will typically carry a medication pen and several pen needles. Each pen needle is designed for safety and sterility. However, inefficiencies and inconveniences arise.

SUMMARY OF THE INVENTION

It is an aspect of the present invention to provide a multiple carrier injection system that provides an improved means to attach a pen needle to a medication delivery pen for use. Such a system provides advantages in accommodating large medication delivery pens to cooperate with small pen needle assemblies. Specifically, the system is able to attach the medication delivery pen to a pen needle disposed in hard-to-access cavities of the multiple carrier injection system.

The foregoing and/or other aspects of the present invention can be achieved by providing a multiple carrier injection system comprising an adapter including at least one arm, a pen needle assembly including a hub retaining a needle, and a bullet (housing) having a cover to seal the bullet, the bullet enclosing the hub in a first position, wherein the arm engages the adapter to the hub, and the arm causes the hub to rotate within the bullet to move the hub into a second position.

The foregoing and/or other aspects of the present invention can also be achieved by providing a method of using a multiple carrier injection system, the method comprising attaching an adapter to a medication delivery pen, engaging the adapter to a hub of a pen needle assembly that is securing a needle, rotating the hub to disengage from the pen needle assembly, piercing a septum of the medication delivery pen via the needle, removing the hub from the pen needle assembly, and dispensing medicament through the needle.

Additional and/or other aspects and advantages of the present invention will be set forth in the description that follows, or will be apparent from the description, or may be learned by practice of the invention.

BRIEF DESCRIPTION OF THE DRAWINGS

The above aspects and features of the present invention will be more apparent from the description for the exemplary embodiments of the present invention taken with reference to the accompanying drawings, in which.

DETAILED DESCRIPTION OF EXEMPLARY EMBODIMENTS

Figure 1:
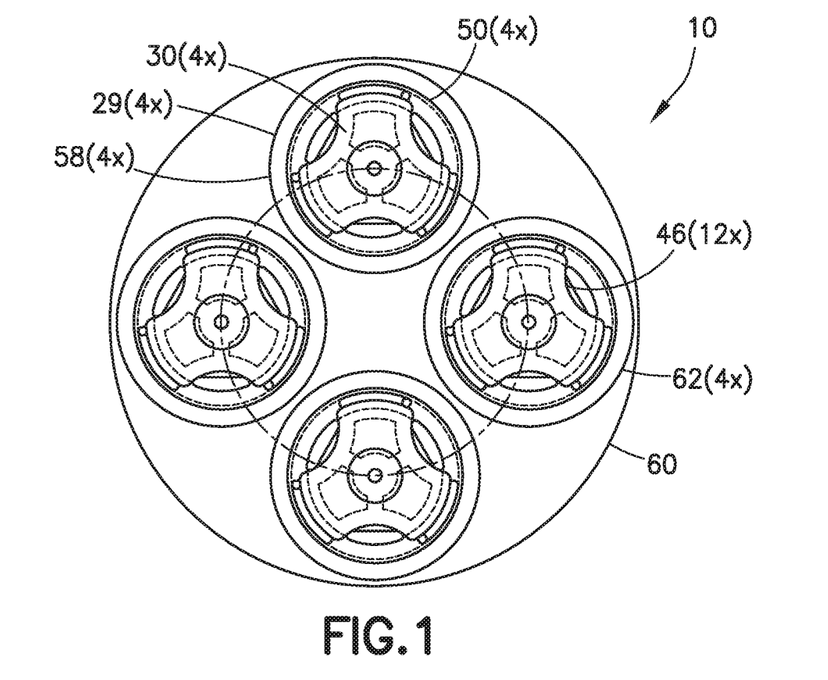
FIG. 1 illustrates a top view of an exemplary pen needle multiple carrier injection system.

FIG. 1 illustrates a multiple carrier injection system 10. The multiple carrier injection system 10 includes a magazine housing 60 that houses a plurality of pen needle assemblies 29.

A cover 58, preferably a foil cover, seals each of the pen needle assemblies 29. The cover 58 provides a sterilized environment for the hub 30 and needle 44 in the pen needle assembly 29. Specifically, the pen needle assembly 29 is assembled, sterilized and sealed with the cover 58 prior to being disposed in the magazine housing 60. The cover 58 can be pierced or peeled off prior to engaging a medication delivery pen (not illustrated but understood to one of ordinary skill in the art) to one of the plurality of pen needle assemblies 29 and commencing operation. Further information regarding the pen needle assemblies 29 are described below.

Figure 2:
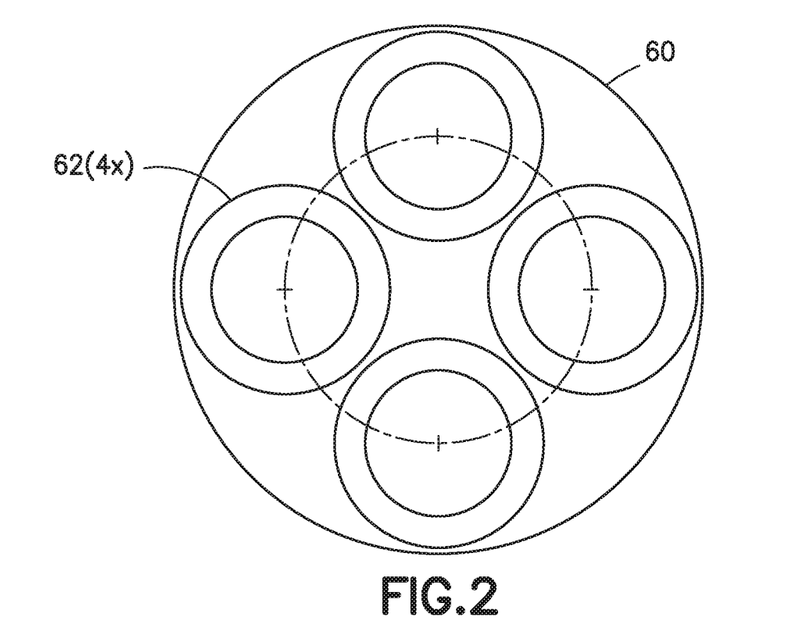
FIG. 2 illustrates a top view of a magazine housing.

FIG. 2 illustrates the magazine housing 60 in the multiple carrier injection system 10. The magazine housing 60 is configured to enclose each of the plurality of pen needle assemblies 29. Four cavities 62 are illustrated, although a magazine housing 60 with more or less cavities 62 is contemplated based on size and weight constraints.

Figure 3:
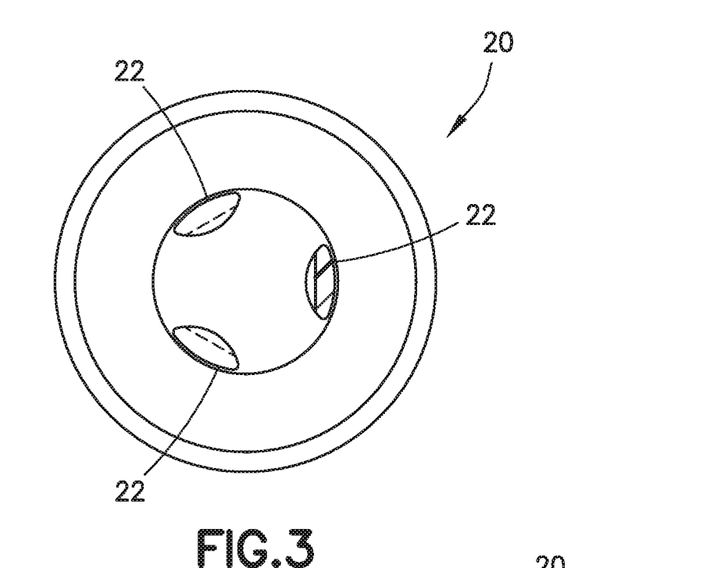
FIG. 3 illustrates a top view of an adapter.

FIG. 3 illustrates a top view of the adapter 20. The adapter 20, also known as a lower vial retainer, is configured to engage the medication delivery pen. Specifically, the proximal end of the adapter 20 includes threads that are configured to mate with threads of the medication delivery pen. Other engagement means between the adapter 20 and the medication delivery pen are contemplated. Alternately, the adapter 20 can be integral to the medication delivery pen.

Figure 4:
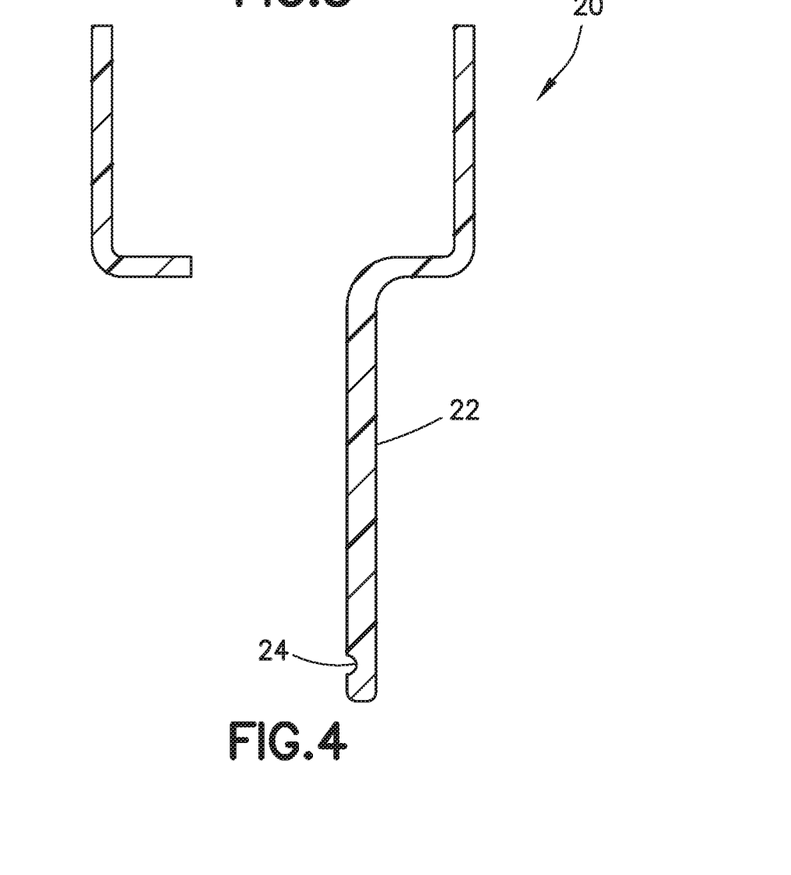
FIG. 4 illustrates a cross sectional view of the adapter of FIG. 3.

The adapter 20, as illustrated in FIG. 4, includes at least one arm 22 that extends from a proximal end of the adapter 20. A plurality of arms 22, such as three, is preferred, although more or less is contemplated. In an alternate configuration, an adapter ring extends from the proximal end of the adapter 20 instead of the plurality of arms 22. However, the plurality of arms 22 advantageously provides a means to pierce the cover 58 when engaging the pen needle assembly 29. An adapter ring configuration at a distal end of the adapter 20 makes it more difficult to pierce the cover 58. This is because each one of the plurality of arms 22 is of a smaller width than an adapter ring and thus provides an improved and more reliable piercing surface.

The plurality of arms 22 is also advantageously configured to engage external contours 46 of a hub 30. This engagement allows the adapter 20 to partially surround and rotationally engage the hub 30. As further described below, the plurality of arms 22 is used to rotate the hub 30 and move the hub 30 in and out of the magazine housing 60.

The adapter 20 further includes a plurality of cavities 24 disposed at a distal end of each of the plurality of arms 22. The plurality of cavities 24 are positioned on an interior surface of each of the plurality of arms 22 to engage each of a plurality of protrusion 40 in the hub 30. The engagement of the plurality of protrusions 40 to each of the plurality of cavities 24 provides a means to advantageously lock the adapter 20 to the hub 30 and remove the hub 30 from a bullet 50 (housing), as further described below. The locking means prevents the hub 30 from being inadvertently removed from the adapter 20 during operation and injection.

Figure 5:
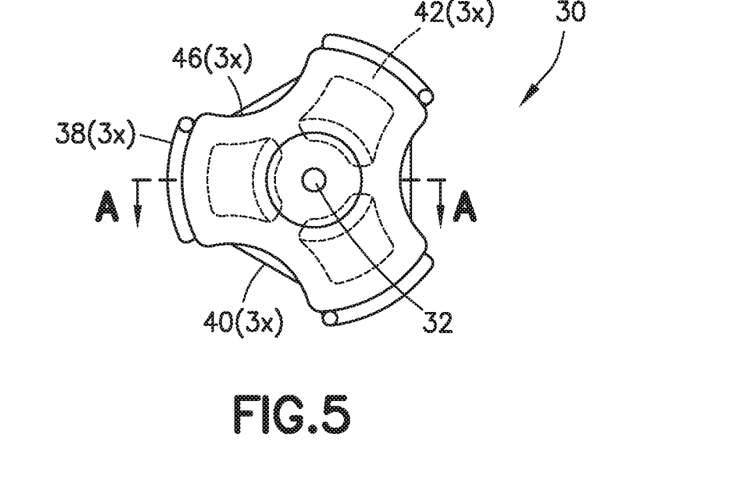
FIG. 5 illustrates a top view of a hub.
Figure 6:
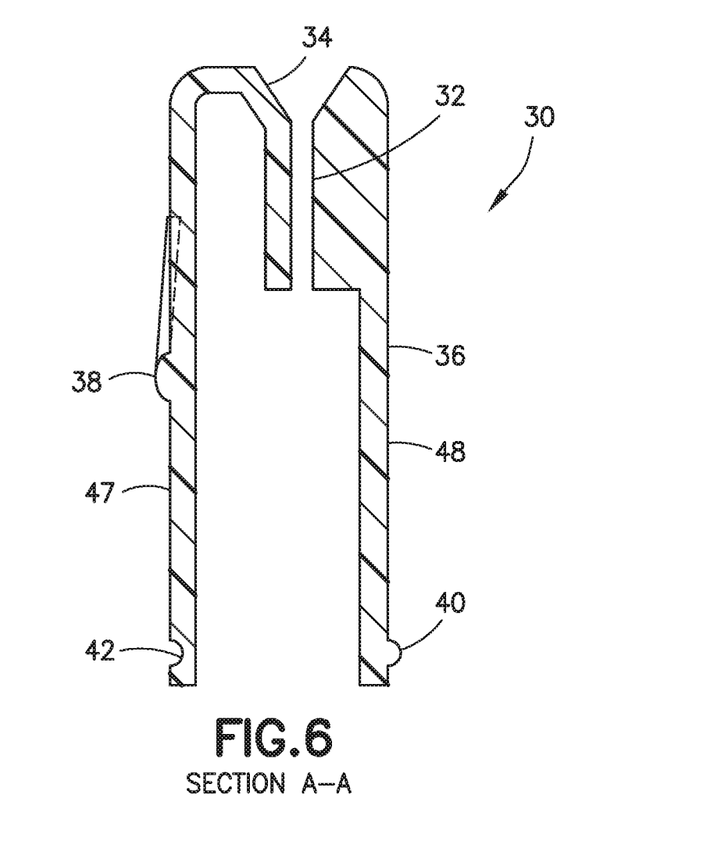
FIG. 6 illustrates a cross sectional view of the hub of FIG. 5 about section A-A.

The multiple carrier injection system 10 includes a plurality of pen needle assemblies 29 each having the hub 30 and the bullet 50. FIGS. 5 and 6 illustrate the hub 30 that secures a needle 44. The needle 44 is retained in a hole 32 of the hub 30. A chamfer 34 or conical surface intersects a proximal end of the hole 32 to advantageously improve assembly of the needle 44 in the hole 32. The hub 30 includes external threads 38 that engage internal threads 52 of a bullet 50 or inner housing, as described in detail below.

External threads 38, the plurality of protrusions 40 and a plurality of recesses 42 are disposed along an external surface of walls 36 of the hub 30. Specifically, the walls 36 of the hub 30 include a plurality of outer legs 47 and a plurality of inner legs 48. The external threads 38 are disposed at a central portion of an outer surface of the plurality of outer legs 47. The plurality of protrusions 40 is disposed at a distal end of the plurality of inner legs 48 while the plurality of recesses 42 is disposed at the distal end of the plurality of outer legs 47. The external threads 38 and the plurality of recesses 42 advantageously prevent the hub 30 from inadvertently disengaging from the bullet 50. On the other hand, the plurality of protrusions 40 engages the plurality of cavities 24 of the adapter 20 to advantageously prevent inadvertent disengagement of the adapter 20 and the hub 30 when the hub 30 is disengaged from the bullet 50.

The hub 30 further includes the external contours 46 disposed along the external surface of the hub 30. The external contours 46 are a curvilinear surface that removes the external thread 38 and the plurality of outer legs 47 at various portions along the external surface of the hub 30. The plurality of inner legs 48 are formed at portions of the external contours 46 where the external thread 38 is not present. The external contours 46 also provides an external cavity for the plurality of arms 22 of the adapter 20 to engage.

Specifically, when the adapter 20 engages the hub 30, the plurality of arms 22 is disposed between the external surface of the hub 30 and the internal surface of the cavity 62 of the magazine housing 60. Also, when the plurality of arms 22 of the adapter 20 engage the external contours 46 of the hub 30, the adapter 20 and the hub 30 are rotationally fixed to each other.

When the hub 30 is disposed in the multiple carrier injection system 10, the hub 30 is in a first position. In the first position, the cover 58 seals the pen needle assembly 29 and the adapter 20 is not engaged to the hub 30. Instead, the hub 30 is engaged to the bullet 50 and secured.

When the hub 30 is removed from the multiple carrier injection system 10 and fully engaged to the adapter 20, the hub 30 is in a second position. In the second position, the plurality of protrusion 40 of the hub 30 engages the plurality of cavities 24 of the adapter 20. Also, the needle 44 pierces a septum of a medication delivery pen when the hub 30 is in the second position. Further explanation of the bullet 50 is described below.

Figure 7:
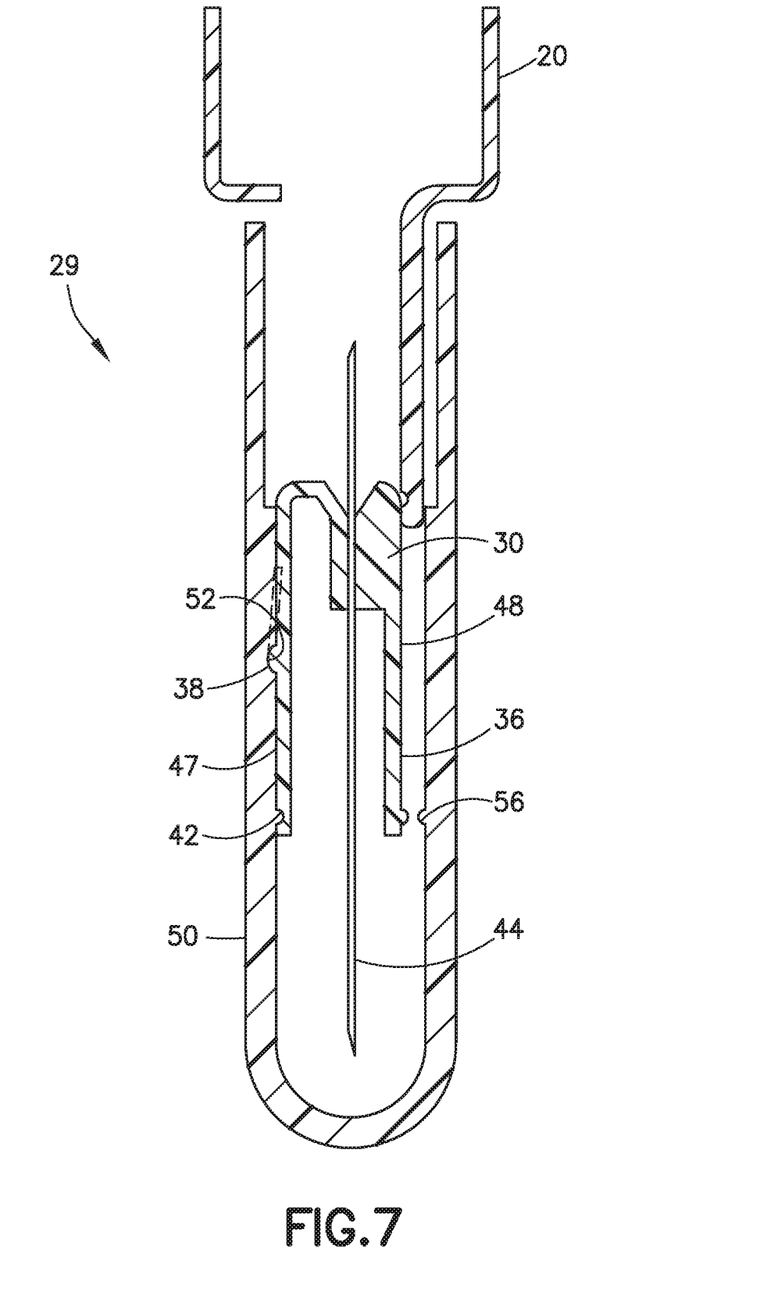
FIG. 7 illustrates a cross sectional view of the adapter engaging a pen needle assembly in a first hub position.
Figure 8:
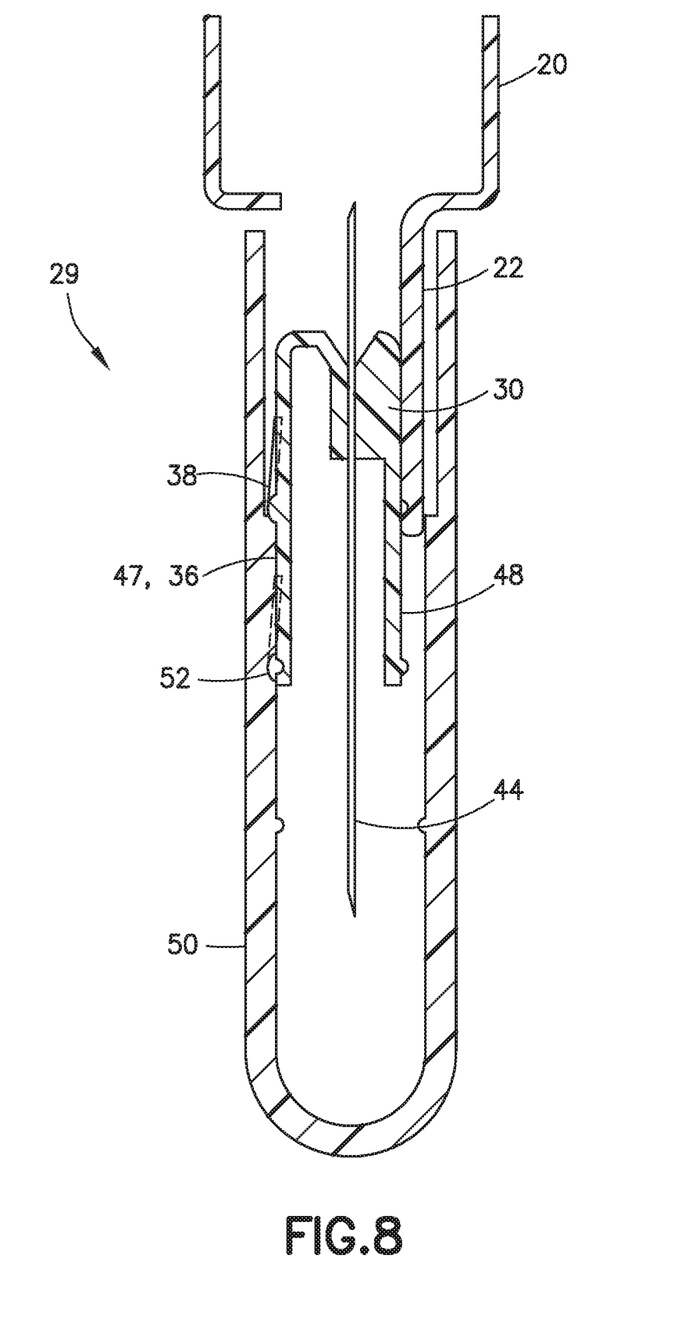
FIG. 8 illustrates a cross sectional view of the adapter engaging the pen needle assembly as the hub leaves the first hub position and travels toward a second hub position.
Figure 9:
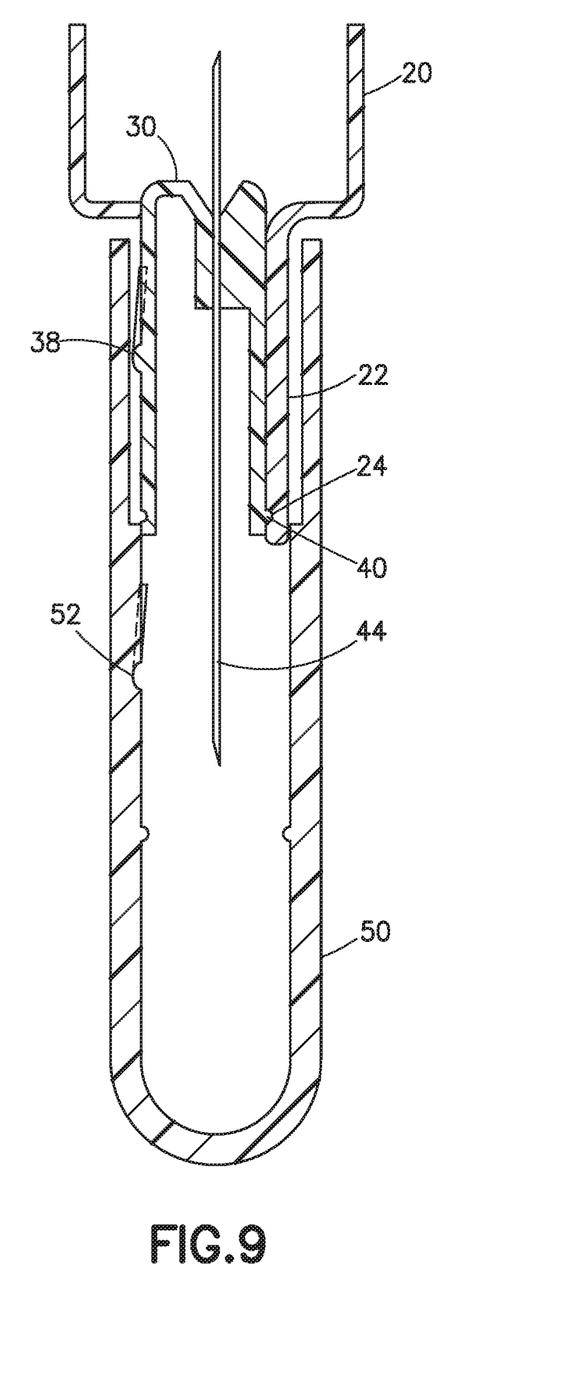
FIG. 9 illustrates a cross sectional view of the adapter engaging the hub of the pen needle assembly in the second hub position.

FIGS. 7-9 illustrate the bullet 50 or pen needle assembly housing. The bullet 50 is a test-tube shaped housing having an interior cavity that encloses the hub 30 and the needle 44. The bullet 50 includes internal threads 52 on an interior surface of the bullet 50. The internal threads 52 engage the external threads 38 of the hub 30. This threaded engagement advantageously allow for rotational and linear movement of the hub 30 with respect to the bullet 50.

The bullet 50 also includes an annular ring or an extruded ring 56 in the internal threads 52. The annular ring 56 engages the plurality of recesses 42 to also advantageously prevent the hub 30 from inadvertently disengaging from the bullet 50. The annular ring 56 in the bullet 50 is engaged to the hub 30 in the first position.

Prior to use, the bullet 50 is threadably engaged to the hub 30, sterilized and sealed by the cover 58 in the first position. The combination of the bullet 50 and hub 30 defines the pen needle assembly 29. A plurality of pen needle assemblies 29 is assembled into the magazine housing 60 to define the multiple carrier injection system 10.

The operation of the multiple carrier injection system 10 is as follows. First, a medical care professional attaches the adapter 20 to a medication delivery pen as commonly understood by one of ordinary skill in the art. Next, the medical care professional uses the arms 22 of the adapter 20 to pierce the cover 58 of one of the pen needle assemblies 29 disposed in the magazine housing 60. As the adapter 20 enters into an interior cavity of the bullet 50, a distal end of the arms 22 engage a proximal end of the external contours 46 of the hub 30. Thus, the adapter 20 and the hub 30 are now rotationally engaged.

The medical care professional subsequently rotates the medication delivery pen and the adapter 20 to remove the hub 30 from the bullet 50. Specifically, as the adapter 20 rotates, the hub 30 also rotates which causes the hub 30 to unthread from the bullet 50. When the external threads 38 of the hub 30 unthreads from the internal threads 52 of the bullet 50, the hub 30 linearly moves upward. FIG. 8 illustrates the hub 30 rotatably translating upward between the first and second positions. As the hub 30 moves upward, the needle 44 pierces the septum of the medication delivery pen.

FIG. 9 illustrates the hub 30 fully disengaged from the bullet 50 in the second position. Specifically, the external threads 38 of the hub 30 are no longer engaged to the internal threads 52 of the bullet 50. Instead, the plurality of cavities 24 of the adapter 20 is engaged to the plurality of protrusions 40 of the hub 30 to advantageously lock the adapter 20 to the hub 30 and allow the hub 30 to be removed from the bullet 50.

In the second position, the needle 44 pierces the septum of the medication delivery pen and the hub 30 is fully engaged to the adapter 20 and the medication delivery pen. The hub 30 can now be removed from the bullet 50. The medication delivery pen is now ready for use by the medical care professional for dispensing medication.

After the medication delivery is complete, the used hub 30 can be disposed in the empty bullet 50 in the magazine housing 60. Specifically, the medical care professional can place the used hub 30 inside the empty bullet 50 and rotate the medication delivery pen to engage the external threads 38 of the hub 30 and the internal threads 52 of the bullet 50. The rotational direction used to return the hub 30 in the bullet 50 from the second position to the first position is an opposite direction than the rotational direction used to remove the hub 30 in the bullet 50 from the first position to the second position. As illustrated in FIG. 1, the medical care professional can now pierce the cover 58 of another pen needle assembly 29 and repeat the process above.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the precise embodiments disclosed. Any of the embodiments and/or elements disclosed herein may be combined with one another to form various additional embodiments not specifically disclosed, as long as they do not contradict each other. Accordingly, additional embodiments are possible and are intended to be encompassed within this specification and the scope of the invention. The specification describes specific examples to accomplish a more general goal that may be accomplished in another way.

As used in this application, the terms "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those of ordinary skill to refer to reasonable ranges outside of the given value, for example, general tolerances associated with manufacturing, assembly, and use of the described embodiments.

The invention claimed is:

1. A multiple carrier injection system comprising:
   an adapter including at least one arm; and
   a pen needle assembly including:
      a hub retaining a needle, the hub comprising a threaded external contour including at least one unthreaded cutout recessed from the threaded external contour, wherein:
         the at least one unthreaded cutout forms an outer leg and an inner leg at an outer surface of the hub; and
         the inner leg is not threaded and the outer leg is threaded; and
      a bullet having a cover to seal the bullet, the bullet enclosing the hub in a first position,
   wherein
      the at least one arm engages the adapter to the at least one unthreaded cutout in the threaded external contour of the hub; and
      the at least one arm causes the hub to rotate within the bullet to move the hub into a second position.

2. The multiple carrier injection system of claim 1, wherein the adapter includes at least three arms.

3. The multiple carrier injection system of claim 2, wherein
   each of the arms rotationally engages the threaded external contour of the hub and pierces the cover; and
   the at least one unthreaded cutout of the threaded external contour includes a plurality of cutouts each corresponding to each of the arms, the plurality of cutouts are not externally threaded.

4. The multiple carrier injection system of claim 1, wherein the at least one arm includes a cavity.

5. The multiple carrier injection system of claim 4, wherein a protrusion of the hub is engaged to the cavity of the adapter in the second position.

6. The multiple carrier injection system of claim 1, wherein
   the hub includes a hole that retains the needle, and
   a proximal end of the hole is chamfered.

7. The multiple carrier injection system of claim 1, wherein
   the outer leg is externally threaded.

8. The multiple carrier injection system of claim 7, wherein the bullet includes internal threads that engage external threads of the outer leg to allow the hub to translate relative to the bullet.

9. The multiple carrier injection system of claim 8, wherein the hub translates rotationally and longitudinally relative to the bullet.

10. The multiple carrier injection system of claim 1, wherein the hub includes a protrusion and a recess.

11. The multiple carrier injection system of claim 10, wherein the bullet includes an annular ring that engages the recess of the hub when the hub is in the first position.

12. The multiple carrier injection system of claim 1, further comprising a magazine housing enclosing a plurality of pen needle assemblies.

13. The multiple carrier injection system of claim 1, wherein the adapter is configured to engage a medication delivery pen.

14. The multiple carrier injection system of claim 1, wherein the adapter is not engaged to the hub in the first position.

15. The multiple carrier injection system of claim 1, wherein the bullet is not engaged to the hub in the second position.

16. The multiple carrier injection system of claim 1, wherein the needle pierces a septum of a medication delivery pen when the hub is in the second position.

17. The multiple carrier injection system of claim 1, wherein the at least one arm rotates to cause the hub to rotationally translate up the bullet into the second position.

18. An assembly comprising:
   a medication delivery pen; and
   the multiple carrier injection system of claim 1, wherein the medication delivery pen is configured to engage and disengage the adapter to engage and disengage any of a plurality of the pen needle assemblies.

19. A method of using a multiple carrier injection system, the method comprising:
   attaching an adapter to a medication delivery pen, the adapter including at least one arm;
   engaging the adapter to a hub of a pen needle assembly that is securing a needle, the hub comprising a threaded external contour including at least one unthreaded cutout recessed from the threaded external contour, the at least one arm engages the adapter to the at least one unthreaded cutout in the threaded external contour of the hub, wherein:
      the at least one unthreaded cutout forms an outer leg and an inner leg at an outer surface of the hub; and
      the inner leg is not threaded and the outer leg is threaded;
   disengaging the hub from the pen needle assembly;
   piercing a septum of the medication delivery pen via the needle;
   removing the hub from the pen needle assembly; and
   dispensing medicament through the needle.

20. The method of claim 19, further comprising
   piercing a cover of the pen needle assembly via the adapter; and
   rotatably engaging the adapter to the hub when the at least one arm engages the at least one unthreaded cutout.

21. The method of claim 19, further comprising rotating the hub to linearly move the hub from a first axial position to a second axial position.

22. The method of claim 19, wherein piercing the septum of the medication delivery pen occurs while rotating the hub to disengage from the pen needle assembly.

23. The method of claim 19, wherein rotating the hub disengages the hub from the pen needle assembly.

24. The method of claim 19, wherein the outer leg is externally threaded.

\* \* \* \* \*